United States Patent [19]

Stoltefuss et al.

[11] Patent Number: 5,650,514
[45] Date of Patent: Jul. 22, 1997

[54] 3-SUBSTITUTED QUINOLINE-5-CARBOXYLIC ACID DERIVATIVES AND PROCESSES FOR THEIR PREPARATION

[75] Inventors: Jürgen Stoltefuss, Haan; Michael Negele, Solingen; Karl-Heinz Wahl, Odenthal; Jan-Bernd Lenfers, Wuppertal; Samir Samaan, Wuppertal, all of Germany

[73] Assignee: Bayer Aktiengesellschaft, Leverkusen, Germany

[21] Appl. No.: 503,168

[22] Filed: Jul. 17, 1995

[30] Foreign Application Priority Data

Jul. 26, 1994 [DE] Germany .......................... 44 26 373.2

[51] Int. Cl.⁶ ..................... C07D 215/14; C07D 215/20; C07D 215/38
[52] U.S. Cl. .......................... 546/153; 546/169; 546/170; 546/173; 546/176
[58] Field of Search ..................... 546/173, 153, 546/170, 176, 169

[56] References Cited

U.S. PATENT DOCUMENTS

| | | | |
|---|---|---|---|
| 4,093,725 | 6/1978 | Roe et al. | 514/248 |
| 5,100,900 | 3/1992 | Stoltefuss et al. | 514/314 |
| 5,204,472 | 4/1993 | Stoltefuss et al. | 546/168 |
| 5,210,231 | 5/1993 | Stoltefuss | 549/304 |
| 5,270,469 | 12/1993 | Stoltefuss | 546/170 |
| 5,476,940 | 12/1995 | Stoltefuss | 546/153 |

FOREIGN PATENT DOCUMENTS

| | | |
|---|---|---|
| 0452712 | 10/1991 | European Pat. Off. . |
| 0476474 | 3/1992 | European Pat. Off. . |
| 0593930 | 4/1994 | European Pat. Off. . |

OTHER PUBLICATIONS

A. Makriyannis, et al., Journal of Medicinal Chemistry, vol. 16, No. 2, (1973), 118–122.
A. Makriyannis, et al., J. Med. Chem., vol. 16, No. 2, pp. 118–122, (1973).
G. Pagani, et al., Farmaco, Ed. Sc., vol. 29, No. 7, pp. 507–516, (1974).
T.S. Tulyaganow, et al., Khim. prir. Soedin., vol. 5, pp. 635–638, (1988).
S.D. Sharma, et al., Indian Journal of Chemistry, vol. 27B, pp. 494–497, 1988.
G. Wagner, et al., Pharmazie, vol. 31, No. 3, pp. 145–148, (1976).
Chemical Abstracts, vol. 114, 130223, 1991.

Primary Examiner—C. Warren Ivy
Assistant Examiner—D. Margaret M. Mach
Attorney, Agent, or Firm—Sprung Horn Kramer & Woods

[57] ABSTRACT

The present invention relates to 3-substituted quinoline-5-carboxylic acid derivatives and processes for their preparation.

11 Claims, No Drawings

3-SUBSTITUTED QUINOLINE-5-CARBOXYLIC ACID DERIVATIVES AND PROCESSES FOR THEIR PREPARATION

The present invention relates to 3-substituted quinoline-5-carboxylic acid derivatives and processes for their preparation.

The publication J. Med. Chem. 16, 118 (1973) discloses the compound ethyl 3-phenylquinoline-5-carboxylate which is obtained by condensation of ethyl 3-aminobenzoate with 1,3-diethoxy-2-phenylpropan-2-ol.

The publications of G. Pagani et al.; Farraaco, Ed. Sci. 29 (7), 507–16 (1974); T. S. Tulyaganow et al.; Khim. Prir. Soedin. (5), 635–8 (1982); S. D. Sharma et al.; Indian J. Chem. Sect. B, 27B (5), 494–7 (1988) disclose some quinoline-N- and N,N-alkylamides. Quinoline-5-carbonitrile too has already been described (in this regard see EP 452 712; Pharmazie, 31 (3), 145- (1976)).

The present invention relates to 3-substituted quinoline-5-carboxylic acid derivatives of the general formula (I)

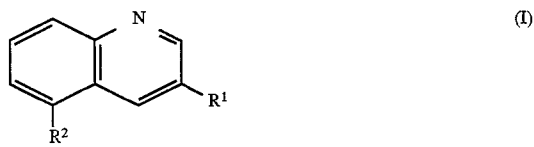

in which
R$^1$ represents straight-chain or branched alkyl having up to 12 carbon atoms, or a radical of the formula —X—R$^3$,
where
X denotes a single bond, an oxygen or sulphur atom or an alkylidene chain having up to 6 carbon atoms,
and
R$^3$ denotes cycloalkyl having from 3 to 8 carbon atoms or phenyl which is optionally substituted identically or differently up to 3 times by nitro, halogen, trifluoromethyl or by straight-chain or branched alkyl, alkoxy or alkoxycarbonyl having in each case up to 8 carbon atoms, hydroxy or carboxy, and
R$^2$ represents a radical selected from the group consisting of —COOCH$_3$, —CN or —CONH$_2$.

Preference is given to compounds of the general formula (I),
in which
R$^1$ represents straight-chain or branched alkyl having up to 10 carbon atoms, or a radical of the formula X—R$^3$,
where
X denotes a single bond, an oxygen or sulphur atom or an alkylidene chain having up to 4 carbon atoms
and
R$^3$ denotes cyclopropyl, cyclopentyl, cyclohexyl or phenyl which is optionally substituted identically or differently up to 2 times by nitro, fluoro, chloro, bromo, trifluoromethyl or by straight-chain or branched alkyl, alkoxy or alkoxycarbonyl each having up to 6 carbon atoms, and
R$^2$ represents a radical selected from the group consisting of —COOCH$_3$, —CN or —CONH$_2$.

Particular preference is given to compounds of the general formula (I),
in which
R$^1$ represents straight-chain or branched alkyl having up to 6 carbon atoms or cyclohexyl, cyclohexylmethyl, cyclopentyl or represents phenyl which is optionally substituted identically or differently up to 2 times by nitro, fluoro, chloro, trifluoromethyl or by straight-chain or branched alkyl, alkoxy or alkoxycarbonyl each having up to 4 carbon atoms, and
R$^2$ represents a radical selected from the group consisting of —COOCH$_3$, —CN or —CONH$_2$.

The compounds of the invention having the general formula (I) are prepared by

[A] in the case of R$^2$=COOCH$_3$, reacting 3-substituted quinoline-5-carboxylic acids of the general formula (II)

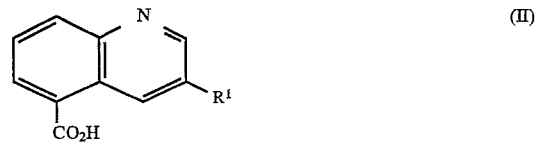

in which
R$^1$ is as defined above, with inorganic or organic acid chlorides such as thionyl chloride or sulphuryl chloride and esterifying the corresponding carboxylic acid chlorides, optionally after isolation, with methanol, or

[B] first reacting carboxylic acid amides of the general formula (III)

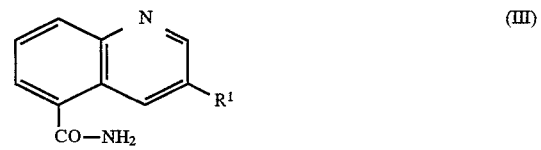

in which
R$^1$ is as defined above, with largely water-free acids in methanol and subsequently precipitating the esters by addition of bases, or

[C] in the case of R$^2$=—CO—NH$_2$, reacting 4-amino-3-hydroxyphthalimidines of the formula (IV)

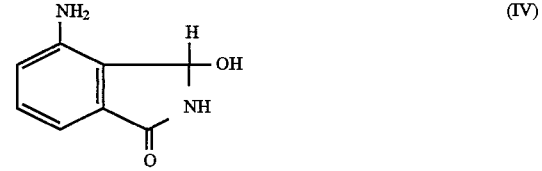

with aldehydes or their acetal derivatives of the general formula (Va) or (Vb)

in which
R$^1$ is as defined above,
R$^4$ and R$^5$ are identical or different and represent cycloalkyl having from 3 to 6 carbon atoms, aryl having from 6 to 10 carbon atoms, or represent straight-chain or branched alkyl having up to 6 carbon atoms, or together represent an ethylene or propylene group, in inert solvents and

[D] in the case of R$^2$=—CN, converting the amides of the formula III, optionally in the presence of inert solvents, into the nitriles by treatment with water-withdrawing agents.

The processes of the invention can be illustrated by way of example by the following reaction schemes:

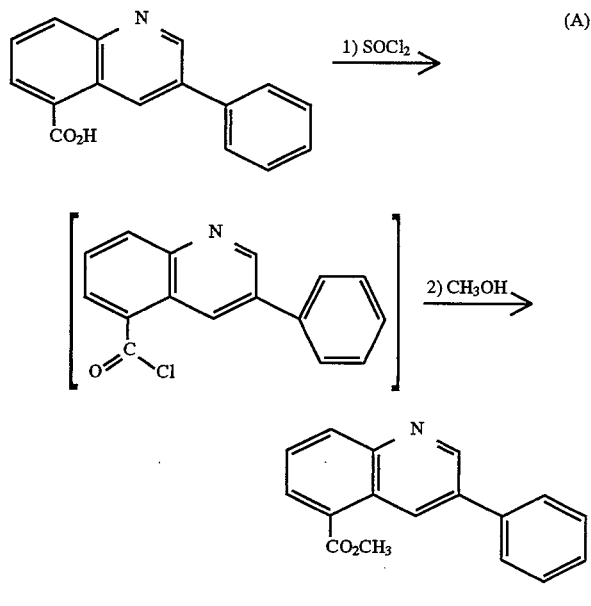

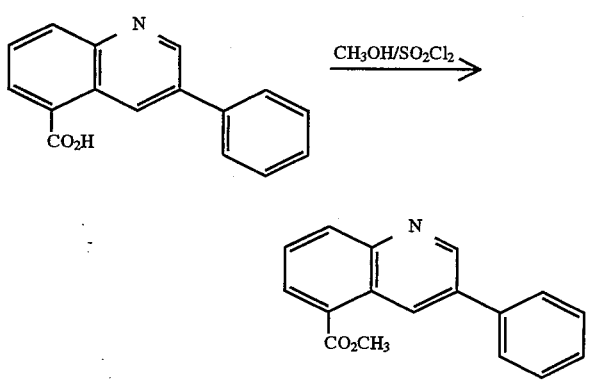

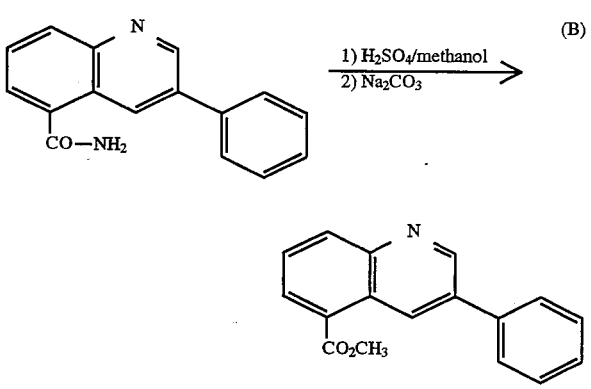

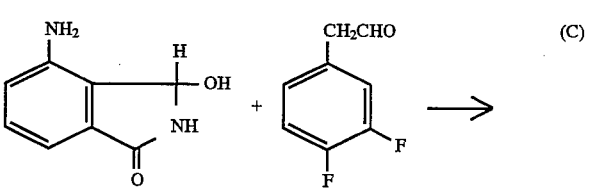

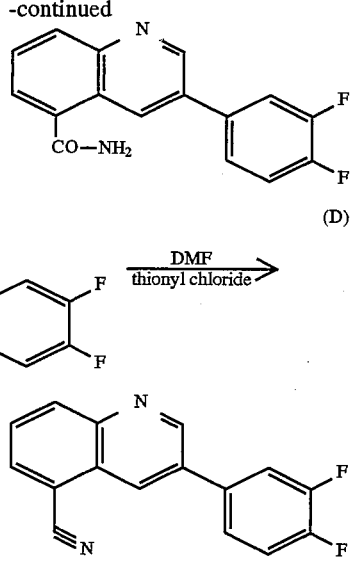

Suitable solvents for the process [A] are, for the first step, all inert organic solvents which do not change under the reaction conditions. These include acetonitrile, or amides such as hexamethylphosphoramide or dimethylformamide, or halogenated hydrocarbons such as methylene chloride, carbon tetrachloride or hydrocarbons such as benzene, chlorobenzene or toluene. It is likewise possible to use mixtures of the specified solvents. Preference is given to dimethylformamide and toluene.

Suitable acid chlorides are generally the customary inorganic or organic acid chlorides such as thionyl chloride, sulphuryl chloride, phosphorus trichloride, phosphorus pentachloride, oxalyl chloride or phthalic acid dichloride. Preference is given to thionyl chloride, sulphuryl chloride and oxalyl chloride. Optionally, the acid chloride can also function as solvent.

The reaction temperatures for the first step can be varied within a wide range. The reaction is generally carried out between +20° C. and +250° C., preferably between 60° C. and 160° C., in particular at the boiling point of the solvent concerned.

The reactions can be carried out at atmospheric pressure, but also at elevated pressure (e.g. from 1 to 100 bar).

In one variant, it is possible to provide the carboxylic acids of the general formula (II) in boiling methanol with a superstoichiometric amount of sulphuryl chloride and, in a second step, to precipitate the methyl ester formed by stirring the reaction mixture into aqueous bases.

Suitable bases are generally alkali metal and alkaline earth metal hydroxides such as, for example, sodium and potassium hydroxide, or alkali metal and alkaline earth metal carbonates such as, for example, sodium and potassium carbonate. Preference is given to sodium hydroxide and sodium carbonate.

The base is generally used in an amount of from 2 mol to 8 mol, preferably from 2 mol to 5 mol, in each case based on 1 mol of the compounds of the general formula (II).

The process [B] is preferably carried out in methanol.

Suitable inorganic acids which are largely water-free are gaseous hydrochloric acid, gaseous hydrogen bromide, concentrated sulphuric acid or concentrated phosphoric acid. Preference is given to reacting concentrated sulphuric acid or HCl gas.

The inorganic acid is used in an amount from 2 mol to 8 mol, preferably from 2 mol to 5 mol, based on 1 mol of the compound of the general formula (IV).

Suitable bases for the precipitation of the corresponding methyl ester are the abovementioned bases in type and amount, based on 1 mol of the amide of the formula (III) adapted to the amount of acid used.

The reaction temperatures can be varied within a relatively wide range. In general, the reaction is carried out at between +20° C. and +250° C., preferably between 40° C. and 160° C., in particular at the boiling point of methanol at atmospheric pressure.

The reactions can be carried out at atmospheric pressure, but also at elevated pressure (e.g. from 1 to 100 bar).

The carboxylic acids of the general formula (II) are known or can be prepared by conventional methods by reacting 4-amino-3-hydroxyphthalide of the formula (VI)

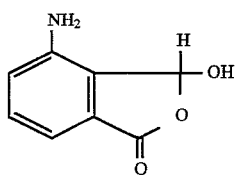 (VI)

with aldehydes of the general formula (Va) or their acetals of the general formula (Vb)

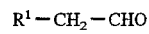 (Va)

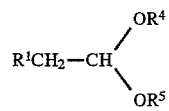 (Vb)

in which $R^1$, $R^4$ and $R^5$ are as defined above, in inert organic solvents.

Suitable solvents are all solvents which are inert under the reaction conditions. Preference is given to methanol, isopropanol, ethanol and n-propanol, acetonitrile, tetrahydrofuran, diethylene glycol dimethyl ether and acetic acid. Particular preference is given to ethanol and isopropanol.

The reaction temperatures can be varied within a relatively wide range. The reaction is generally carried out at between +20° C. and +150° C., preferably between +60° C. and +120° C., in particular at the boiling point of the solvent concerned.

The reaction can be carried out at atmospheric pressure, but also at elevated pressure (e.g. from 1 to 50 bar). It is generally carried out at atmospheric pressure.

The compound of the general formula (VI) is known [cf. EP 476 474 A1].

The aldehydes and their acetals of general formulae (Va) and (Vb) are known in some cases or can be prepared by known methods.

Suitable solvents for the process [C] are here all inert organic solvents which do not change under the reaction conditions and their mixtures with water. These include alcohols such as methanol, ethanol, propanol, isopropanol or ethylene glycols, or ethers such as dioxane, tetrahydrofuran, glycol dimethyl ether, or diethylene glycol dimethyl ether, acetonitrile, or amides such as hexamethylphosphoramide or dimethylformamide, or acetic acid or halogenated hydrocarbons such as methylene chloride, carbon tetrachloride or hydrocarbons such as benzene, chlorobenzene or toluene, and also esters such as, for example, ethyl acetate. It is likewise possible to use mixtures of the specified solvents. Preference is given to dimethylformamide, acetic acid, acetic acid/water, chlorobenzene or diethylene glycol dimethyl ether. It is also possible to carry out the reaction in the respective aldehyde or acetal as solvent. Particular preference is given to acetic acid or mixtures of acetic acid with water.

The reaction temperatures for the first step can be varied within a relatively wide range. The reaction is generally carried out at between +20° C. and +250° C., preferably between 60° C. and 160° C., in particular at the boiling point of the solvent concerned.

The reactions can be carried out at atmospheric pressure, but also at elevated pressure (e.g. from 1 to 100 bar).

The 4-amino-3-hydroxyphthalimidine of the formula (IV) is new and can be prepared, for example, by reducing, preferably by hydrogenation, the known 4-nitro-3-hydroxyphthalimidine by conventional methods in inert solvents in the presence of a catalyst.

Suitable solvents for the process [D] ($R^2$=CN) are, in particular, dimethylformamide or dimethyl sulphoxide. However, it is also possible to use the respective water-withdrawing agent as solvent.

Suitable water-withdrawing agents are, for example, phosphorus pentoxide, phosphoryl chloride, phosphorus pentachloride or thionyl chloride. Preference is given to thionyl chloride.

The reaction temperatures for the second step are generally in a range from −20° C. to +50° C., preferably at 0° C.–+25° C.

The reactions can be carried out at atmospheric pressure, but also at elevated pressure (e.g. from 1 to 100 bar).

The above preparation processes are given merely for clarification. The preparation of the compounds of the invention having the general formula (I) is not limited to these processes, but any modification of these processes can be used in the same manner for the preparation of the compounds of the invention.

The 3-substituted quinoline compounds of the invention are of great importance to 1,4-dihydropyridine chemistry, since they are valuable intermediates for the synthesis of 4-quinolyl-dihydropyridines [in this respect see, for example, EP 452 712].

PREPARATIVE EXAMPLES

Example 1

Methyl 3-phenylquinoline-5-carboxylate

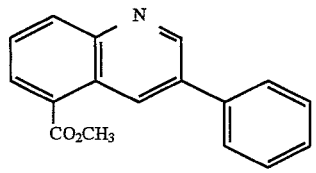

1a. Process A: (1st variant)

A solution of 67.5 ml of thionyl chloride (0.93 mol) in 300 ml of toluene is added dropwise at 70° C.–75° C. to a suspension of 187.5 g of 3-phenylquinoline-5-carboxylic acid (0.75 mol) in 1500 ml of toluene over a period of 30 minutes. The mixture is then stirred under reflux for 2 hours, with the temperature rising to about 110° C. After cooling to 60° C., 150 ml of methanol are added dropwise over a period of 10 minutes (slightly exothermic reaction). The mixture is stirred for a further 30 minutes under reflux (about 75° C.) and then cooled to room temperature. A solution of 150 g of sodium carbonate in 900 ml of water is allowed to run into the mixture. The pH must now be from 9.0 to 9.5. The mixture is left stirring for 30 minutes at about 40° C. and the toluene phase is separated off. This solution is dried over $Na_2SO_4$ and, after filtration, is, in accordance with the use example (variant a) changed over to tert-butanol by taking off the toluene.

1b. Process A: (2nd variant)

249.3 g (1 mol) of 3-phenylquinotine-5-carboxylic acid are suspended while stirring at about 50° C. in 2 l of methanol (technical grade). 136 ml of sulphuryl chloride (1.7 mol) are added dropwise at about 50°–60° C. over a period of about 2 hours (exothermic reaction, remove heating bath). After the addition is complete, the mixture is boiled under reflux overnight and subsequently cooled to room temperature. The reaction mixture is added dropwise to a solution of 188 g (1.77 mol) of $Na_2CO_3$ in 2 l of water over a period of about 15 minutes; the precipitate is filtered off with suction, washed free of salts using 500 ml of water and dried overnight in vacuo at 60° C.

Yield: 253 g (96% of theory)

Mp.: 99°–100° C.

1c. Process B 248.0 g (1 mol) of 3-phenylquinoline-5-carboxamide are suspended while stirring under reflux in 2.0 l of methanol (technical grade). 300 ml of concentrated $H_2SO_4$ are added dropwise over a period of about 2 hours. The mixture is subsequently stirred further under reflux for about 4–5 hours; a clear solution is formed. For the work-up, the solution, cooled to room temperature, is stirred into 4 l of ice-cold aqueous sodium carbonate solution (about 4 molar). The methyl ester is precipitated, is stirred for a further 1 hour and filtered off with suction. The filter cake is washed to neutrality using 500 ml of $H_2O$ and subsequently dried in vacuo at about 80° C. overnight.

Yield (crude): 262 g (99.5% of theory)

The crude product is recrystallized from 2 l of methanol.

Yield (after drying): 204 g (77.5% of theory)

Mp.: 99°–100° C.

Example 2

3-Phenylquinoline-5-carboxamide

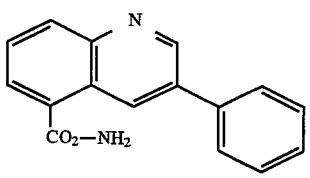

Process (C)

a) 3.28 g (20 mmol) of 4-amino-3-hydroxyphthalimidine are suspended in 40 ml of diglyme and admixed with 4 ml of phenylacetaldehyde. The mixture is stirred for 1 hour at a bath temperature of 170° C., giving a clear solution and then precipitating a byproduct. The mixture is filtered with suction while hot. The filtrate is admixed with 5 ml of water and cooled while stirring. The precipitated crystals are filtered off with suction, washed with water and ethanol and dried. This gives 2.6 g (52.4% of theory) of colourless crystals having a melting point of 227°–229° C.

b) 492.5 g (3 mol) of 4-aminophthalimidine (crude material, contains catalyst) are suspended in 3 l of glacial acetic acid and heated to reflux (115° C.). While stirring, 497 ml (3 mol) of phenylacetaldehyde dimethylacetal are added dropwise over a period of about 30 minutes. The mixture is subsequently stirred further for about 6 hours under reflux, giving an almost clear solution (apart from the catalyst). The reaction mixture is filtered hot (about 80° C.) and then slowly cooled to room temperature while stirring. The crystal mass which forms is filtered off with suction, washed with about 500 ml of glacial acetic acid and then with about 100 ml of water. It is dried for 48 hours at from about 70° to 80° C. in vacuo.

Yield: 383 g (65% of theory)

Example 3

3-n-Hexylquinoline-5 -carboxamide

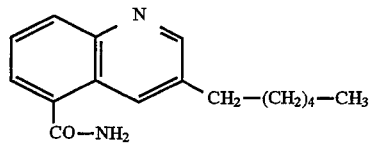

1.64 g (5 mmol) of 4-amino-3-hydroxyphthalimidine are admixed in 15 ml of diglyme with 2 ml of octanal and stirred for 4 hours at a bath temperature of 160° C.

The mixture is cooled, poured into iced water, filtered with suction and the solid is washed with water and petroleum ether. The residue is stirred with 10 ml of warm DMF and filtered off from the insoluble residue. The filtrate is separated by flash chromatography using toluene/acetone mixtures. The fractions containing the desired compound are evaporated. Crystallization using acetonitrile gives 130 mg (about 10%) of colourless crystals having a melting point of from 206° to 208° C.

Example 4

3-Phenylquinoline-5-carbonitrile

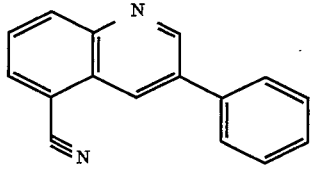

124 g (0.5 mol) of the compound from Example 2 (3-phenylquinoline-5-carboxamide) are initially charged in 500 ml of DMF at room temperature. While stirring, 90 ml of thionyl chloride are added dropwise while cooling in ice, the internal temperature is maintained at between 20° and 25° C. The mixture is stirred further for 2.5 hours, 100 ml of water is then added dropwise and the suspension is stirred into 1500 ml of dilute sodium hydroxide solution (2.5N). The temperature is maintained at about 30° C. by means of ice cooling. The crystalline product is filtered off with suction, washed with water and dried in vacuo.

Yield: 98 g (i.e. 85% of theory)

IR (KBr): $v=2220$ cm$^{-1}$ (v, CN).

Use Examples (Preparation of 3-phenylquinoline-5-carbaldehyde)

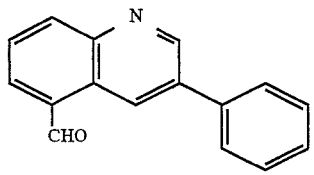

Variant a 200 g (0.75 mol) of the compound as described in Example 1c (methyl ester) are dissolved in 1500 ml of tert-butanol. 75 g of sodium borohydride (2 mol) are introduced into this solution. 400 ml of methanol are then added dropwise at 70°–75° C. over a period of 3 hours ($H_2$ evolution). The mixture is left stirring further for 30 minutes under reflux. 50 ml of acetone are then added dropwise, and the mixture is stirred for a further one hour under reflux. A mixture of 450 ml of water and 50 ml of concentrated sodium hydroxide solution is then allowed to run into the mixture. The solvent is distilled off under atmospheric pressure up to an internal temperature of 98°–100° C. (about 2000 ml). After addition of 250 ml of water, the mixture is extracted four times at 50°–60° C. with 300 ml of toluene each time. Small amounts of tarry components should remain in the aqueous phase. The combined toluene solutions are evaporated under atmospheric pressure to a residual volume of about 700 ml and added dropwise to a suspension of 660 g of manganese dioxide in 600 ml of toluene. The mixture is then stirred for 3 hours at 45°–50° C. After complete oxidation (monitoring by HPLC), the manganese dioxide is filtered off with suction and washed with toluene. The toluene is largely distilled off under reduced pressure. After addition of 650 ml of isopropanol, the precipitated product is dissolved under reflux. 150 ml of solvent are distilled off under atmospheric pressure. The mixture is cooled to 0° C. and stirred for 2 hours at 0° C. The product is filtered off with suction, washed with 50 ml of cold isopropanol and dried in vacuo at 30° C.

Yield: 113 g (64.6% of theory)

Variant b 23 g (0.1 mol) of 3-phenylquinoline-5-carbonitrile (substance from Example 4) are admixed in 150 ml of formic acid with 10 g of Raney nickel. The mixture is stirred for about 5 hours at about 80° C. The slow formation of 3-phenylquinoline-5-carbaldehyde is observed by means of HPLC. In addition, 3-phenyl-5-hydroxymethylquinoline is formed as overreduced product. For the work-up, 300 ml of $H_2O$ are stirred in and the mixture is optionally extracted with 200 ml of methylene chloride. The methylene chloride phase is subsequently stirred at 40° C. (reflux) for 2 hours with 10 g of manganese dioxide. After filtration, the solution is evaporated and the residue is recrystallized from isopropanol.

Yield: 13.5 g (=58% of theory).

We claim:

1. A methyl 3-substituted-quinoline-5-carboxylic acid ester compound of the formula:

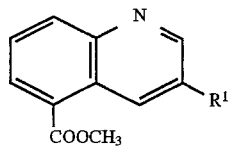

wherein $R^1$ represents straight-chain or branched alkyl having up to 6 carbon atoms or cyclohexyl, cyclohexylmethyl, or cyclopentyl, or phenyl which is optionally substituted identically or differently up to 2 times by nitro, fluoro, chloro, trifluoromethyl or by straight-chain or branched alkyl, alkoxy or alkoxycarbonyl each having up to 4 carbon atoms.

2. A compound according to claim 1, which is methyl 3-phenylquinoline-5-carboxylate of the formula:

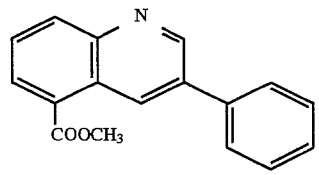

3. A 3-substituted-quinoline-5-carboxamide compound of the formula:

wherein $R^1$ represents straight-chain or branched alkyl having up to 6 carbon atoms or cyclohexyl, cyclohexylmethyl, or cyclopentyl, or phenyl which is optionally substituted identically or differently up to 2 times by nitro, fluoro, chloro, trifluoromethyl or by straight-chain or branched alkyl, alkoxy or alkoxycarbonyl each having up to 4 carbon atoms.

4. A compound according to claim 3, which is 3-phenylquinoline-5-carboxamide of the formula:

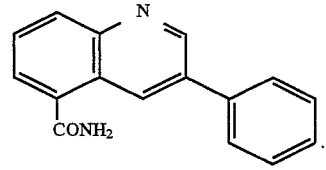

5. A compound according to claim 3, which is 3-n-hexylquinoline-5-carboxamide of the formula:

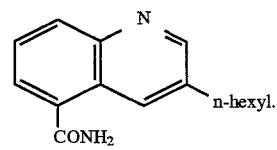

6. A process for preparing a quinoline-5-carbaldehyde of the formula

[Structure: quinoline with CHO substituent and R¹]

wherein

R¹ represents straight-chain or branched alkyl having up to 6 carbon atoms or cyclohexyl, cyclohexylmethyl, or cyclopentyl, or phenyl which is optionally substituted identically or differently up to 2 times by nitro, fluoro, chloro, trifluoromethyl or by straight-chain or branched alkyl, alkoxy or alkoxycarbonyl each having up to 4 carbon atoms, which comprises reacting in an inert solvent a compound of the formula

[Structure with NH₂, H, OH, NH, and C=O groups] (IV)

with an aldehyde of the formula

R¹—CH₂—CHO        (Va)

in which

R¹ is defined above, and the amide of the formula

[Quinoline structure with CO—NH₂ and R¹]        (III)

thus obtained into the methyl ester derivative of the formula

[Quinoline structure with COOCH₃ and R¹]

in the presence of a largely water-free acid in methanol and subsequently precipitating the ester thus formed by the addition of a base and subsequently converting the methyl ester derivative obtained above into the quinoline-5-carbadehyde product by first reacting the methyl ester derivative with NaBH₄ followed by an oxidation with MnO₂.

7. The process according to claim 6, wherein the largely water-free acid is $H_2SO_4$ and the base is $Na_2CO_3$.

8. A process for the preparation of a compound according to claim 1, which comprises reacting a 3-substituted quinoline-5-carboxylic acid of the formula

[Quinoline structure with CO₂H and R¹]        (II)

in which

R¹ represents straight-chain or branched alkyl having up to 6 carbon atoms or cyclohexyl, cyclohexylmethyl, or cyclopentyl, or phenyl which is optionally substituted identically or differently up to 2 times by nitro, fluoro, chloro, trifluoromethyl or by straight-chain or branched alkyl, alkoxy or alkoxycarbonyl each having up to 4 carbon atoms, in the presence of an inorganic or an organic acid chloride and after optionally isolating the corresponding carboxylic acid chloride intermediate, esterifying said intermediate with methanol.

9. A process for the preparation of a compound according to claim 3, which comprises reacting a 3-carboxylic acid amide of the formula

[Quinoline structure with CO—NH₂ and R¹]        (III)

in which

R¹ represents straight-chain or branched alkyl having up to 6 carbon atoms or cyclohexyl, cyclohexylmethyl, or cyclopentyl, or phenyl which is optionally substituted identically or differently up to 2 times by nitro, fluoro, chloro, trifluoromethyl or by straight-chain or branched alkyl, alkoxy or alkoxycarbonyl each having up to 4 carbon atoms, in the presence of a largely water-free acid in methanol and subsequently precipitating the 3-carboxylic acid amide with the addition of a base.

10. The method according to claim 9, wherein the largely water-free acid is gaseous HCl, gaseous HBr, concentrated $H_2SO_4$ or concentrated $H_3PO_4$.

11. The method according to claim 9, wherein the base is an alkali metal hydroxide, an alkaline earth hydroxide, an alkali metal carbonate, or an alkaline earth metal carbonate.

* * * * *